United States Patent [19]
Ando et al.

[11] Patent Number: 4,713,245
[45] Date of Patent: Dec. 15, 1987

[54] GRANULE CONTAINING PHYSIOLOGICALLY-ACTIVE SUBSTANCE, METHOD FOR PREPARING SAME AND USE THEREOF

[75] Inventors: Shinji Ando; Masami Ohtaguro, both of Nagoya; Takayoshi Masuda, Tohkai; Yoshimoto Watanabe, Kasugai, all of Japan

[73] Assignee: Mitsui Toatsu Chemicals, Incorporated, Tokyo, Japan

[21] Appl. No.: 737,407

[22] Filed: May 24, 1985

[30] Foreign Application Priority Data

| Jun. 4, 1984 | [JP] | Japan | 59-113192 |
| Jun. 4, 1984 | [JP] | Japan | 59-113193 |
| Jul. 31, 1984 | [JP] | Japan | 59-159193 |

[51] Int. Cl.$^4$ ................................ A61K 9/42
[52] U.S. Cl. .................... 424/438; 424/439; 424/442; 424/476; 424/482; 424/498; 424/502; 426/2; 426/807; 427/3
[58] Field of Search ............ 424/38, 438, 439, 442, 424/476, 482, 498, 502; 427/3; 426/2, 807

[56] References Cited

U.S. PATENT DOCUMENTS

| 3,374,146 | 3/1968 | Blicharz et al. | 424/19 |
| 3,541,204 | 11/1970 | Sibbald et al. | 424/38 |
| 3,670,065 | 6/1972 | Ericksson et al. | 424/19 |
| 3,726,805 | 4/1973 | Mackawa et al. | 424/38 |
| 3,798,338 | 3/1974 | Galle | 424/38 |
| 3,804,776 | 4/1974 | Yazawa et al. | 424/38 |
| 3,959,493 | 5/1976 | Baalsrud et al. | 424/38 |
| 3,960,757 | 6/1976 | Morishita et al. | 424/38 |
| 4,102,806 | 7/1978 | Kondo et al. | 424/38 |
| 4,132,753 | 1/1979 | Blichare et al. | 424/38 |
| 4,483,847 | 11/1984 | Augart | 424/38 |

Primary Examiner—Shep K. Rose
Attorney, Agent, or Firm—Fisher, Christen & Sabol

[57] ABSTRACT

Disclosed herein is a granule containing physiologically-active substance which comprises at least (A): a physiologically-active substance;
(B): a substance which is stable under neutral condition but disintegrates or dissolves at a pH of 3 or less; and
(C): at least one substance selected from the group consisting of straight-chain or branched, saturated or unsaturated monocarboxylic acids having at least 14 carbon atoms and salts thereof, animal fats having a melting point of 40° C. or higher, vegetable fats having a melting point of 40° C. or higher and waxes having a melting point of 40° C. or higher, and which granule further has a protective film comprising at least said substances (B) and (C) on the surface thereof. The protective film has a thickness of preferably at most 20% of the granular diameter and is preferably at least composed of at least 10% by weight of the substance (B) and at most 90% by weight of the substance (C). Granules having this specific protective film on the surface thereof have the use as a feed additive composition. A method for preparing said granules is also disclosed.

6 Claims, No Drawings

GRANULE CONTAINING PHYSIOLOGICALLY-ACTIVE SUBSTANCE, METHOD FOR PREPARING SAME AND USE THEREOF

BACKGROUND OF THE INVENTION

1. Field of the Invention

This invention relates to granules containing physiologically-active substance, a method for preparing the same and the use thereof. More specifically, this invention relates to granules having such characteristics that a physiologically-active substance or substances contained therein are retained stably under neutral condition and dissolved out therefrom under acidic condition, a method for preparing the same and the use thereof as a feed additive composition.

In the present invention, the term "neutral condition" means a condition having a pH of 5-8 which is equivalent to a condition in the rumen of a ruminant and a condition in the buccal cavity and oesophagus of a mono-gastric animal.

2. Description of the Prior Art

Granules having such properties that a physiologically-active substance or substances contained therein are retained stably under neutral condition but dissolved out under acidic condition are highly useful for living bodies. For example, their usefulness, especially for ruminants, has lately attracted considerable attention.

A ruminant allows a variety of microorganisms to live in its rumen under neutral condition and makes use of their activities to digest and use ingredients such as cellulose, which cannot inherently be digested by a mono-gastric animal. Through physiological and/or nutriological researches on ruminants, the existence of rumens have been pointed out as one of causes for the limited productivity of ruminants in recent years. As a result, a great deal of work is now under way with a view toward allowing a physiologically-active substance, the consumption of which in the rumen is not desired, to pass through the rumen substantially unaltered and to undergo disintegration and absorption in the abomasum and its subsequent digestive tract so that the physiologically-active substance can be used more efficiently. Thus, there has been long-awaited a technique for preparing granules which allow a physiologically-active substance to be retained stably under neutral condition (in rumen) and to dissolve under acidic condition (in abomasum) from the viewpoint of the efficient breeding of ruminants. Such a technique is also useful for physiologically-active substances which are expected to dissolve in the stomach of a mono-gastric animal.

There have already been proposed several methods in relation to the technique which permits substantially unaltered passage of physiologically-active substances through the rumen of ruminants. However, none of the methods appear to be fully effective. For example, German Pat. No. 2212568 discloses granules composed of a biologically-effective substance coated with a film comprising an aliphatic monocarboxylic acid having 14–22 carbon atoms, ricinoleic acid or a mixture thereof, or with a film comprising a salt of each of said acids or a mixture thereof. Japanese Patent Publication No. 45224/1974 discloses a method for preparing an capsule of a fat containing an amino acid which method comprises dispersing an amino acid or polypeptide into a melt mixture consisting of a fat having a melting point of 40° C. or higher and a fat having a melting point lower than 40° C. and pouring the resulting dispersed mixture into water kept at a temperature between 20° C. and 40° C.

Japanese patent publication No. 1057/1981 discloses a biologically-active substance coated with a matrix formed of a saturated, straight-chain or branched, substituted or unsubstituted, aliphatic monocarboxylic acid having at least 14 carbon atoms or salt thereof or a mixture of said saturated acid or its salt and an unsaturated, straight-chain or branched, substituted or unsubstituted, aliphatic monocarboxylic acid having at least 14 carbon atoms or a salt thereof.

Japanese Patent Laid-open No. 154956/1981 discloses a biologically-effective granular substance equipped with a coating film containing an aliphatic monocarboxylic acid having 14-22 carbon atoms or a mixture of salts of some of aliphatic monocarboxylic acids having 14-22 carbon atoms. Reference may also be made to Japanese Patent Laid-open No. 175449/1983, which discloses a biologically-active substance enclosed by a coating film of a protective material which contains one or more substances selected from the group consisting of straight-chain or branched, saturated or unsaturated monocarboxylic acids, hydrogenated vegetable fats and hydrogenated animal fats, and chitosan.

The techniques of German Pat. No. 2212568, Japanese patent publication No. 45224/1974 and Japanese patent publication No. 1057/1981 are accompanied by such drawbacks that the time available for the digestion and absorption is too short to achieve sufficient digestion and absorption, because it is primarily intended to effect the degradation of the coating material in the small intestine and its subsequent digestive tract. In Japanese Patent Laid-open Nos. 154956/1981 and 175449/1983, there are used, with a view toward overcoming the above-mentioned drawbacks, such coating materials that disintegrate to allow one or more substances, effective for the living body, to dissolve out in the abomasum. However, the effectiveness of the techniques cannot be considered to be stable since the degradation of the coating materials in the abomasum does not proceed sufficiently.

Thus, in the existing state of art, there are no satisfactory granules which allow the physiologically-active substance contained therein to be retained stably in the rumen (under neutral condition) and to leach out therefrom in the abomasum (under acidic condition). Therefore, it is the real state of affairs that there is still no satisfactory feed additive compositions capable of passing through the rumen substantially unaltered and dissolving out in the abomasum and its subsequent digestive tract.

SUMMARY OF THE INVENTION

An object of the present invention is to provide an improved granule containing physiologically-active substance which granule is stable under neutral condition and disintegrates or dissolves under acidic condition and a method for preparing the same.

Another object of the present invention is to provide an improved feed additive composition capable of passing through the rumen substantially unaltered and dissolving in the abomasum of ruminants.

Other objects of the present invention will become appearent by the description below.

In accordance with the present invention, there is provided a granule containing physiologically-active substance comprising at least (A): a physiologically-active substance;
(B): a substance which is stable under neutral condition but disintegrates or dissolves at a pH of 3 or less; and
(C): at least one substance selected from the group consisting of straight-chain or branched, saturated or unsaturated monocarboxylic acids having at least 14 carbon atoms and salts thereof, animal fats having a melting point of 40° C. or higher, vegetable fats having a melting point of 40° C. or higher and waxes having a melting point of 40° C. or higher, said granule having a protective film comprising at least said substances (B) and (C) on the surface thereof.

The protective film comprises preferably at least 10% by weight of the substance (B) and at most 90% by weight of the substance (C) and constitutes the surface layer portion preferably having a thickness of 20% or less of the granular diameter.

DETAILED DESCRIPTION OF THE INVENTION

The term "physiologically-active substance (A)" as used herein may mean, in the case of a ruminant, for example, nourishment, livestock feed containing nourishment and/or drugs which are desirably absorbed at the abomasum and its subsequent digestive tract into the body of the ruminant per se without being consumed by microorganisms in the rumen. On the other hand, in the case of a mono-gastric animal, it means nourishment and drugs which are desirably dissolved in the stomach.

Illustrative of such substances includes amino acids, amino acid derivatives, proteins, vitamins, enzymes, carbohydrates, drugs for animal use, hormons, etc. Specific examples thereof are: as amino acids, methionine, lysine, threonine, leucine, isoleucine, tryptophan, phenylalanine, valine and glycine; as amino acid derivatives, for example, N-acylamino acids, e.g., N-stearoylmethionine, N-oleoylmethionine, the calcium salt of N-hydroxymethylmethionine, lysine hydrochloride, methionine hydroxy analogues and sodium glutamate; as proteins, feather meal, fish meal, casein, corn protein and potato protein; as vitamins, vitamin A, vitamin A palmitate, vitamin A acetate, β-carotene, vitamin $D_2$, vitamin $D_3$, vitamin E, menadion sodium bisulfite, a group of vitamin B's (thiamine, thiamine hydrochloride, riboflavin, nicotinic acid, nicotinic acid amide, calcium pantothenate, choline pantothenate, pyridoxine hydrochloride, choline chloride, cyanocobalamin, biotin, folic acid and p-aminobenzoic acid; as enzymes, protease preparation, amylase preparation, mixed enzyme preparation and lipase preparation; as carbohydrates, starch, glucose and sucrose; as drugs for animal use, antibiotics such as tetracyclines, aminoglycosides, macrolides, polypeptides, polysaccharides and polyethers, vermifuges such as Negphone, and antiparasitics such as piperazine salts; and as hormones, estrous hormones such as estrogen, stilbestrol and hexestrol, and thyroid hormones such as thyroprotein and goitrogen.

Although these substances are generally used alone, they may also be used in combination as a mixture.

These physiologically-active substances may be contained in the surface layer portion. It is however more preferred in view of the stability of the physiologically-active substances in the rumen that they are not contained in the surface layer portion.

Specific examples of the substance (B), which is stable under neutral condition but disintegrates or dissolves at a pH of less than 3, for example, under acidic condition of hydrochloric acid, include cellulose derivatives such as benzylaminomethyl cellulose, dimethylaminomethyl cellulose, piperidylethylhydroxyethyl cellulose, cellulose acetate diethylaminoacetate, cellulose acetate and dibutylaminohydroxypropylether; polyvinyl derivatives such as vinyldiethylamine-vinyl acetate copolymer, vinylbenzylamine-vinyl acetate copolymer, polyvinyldiethylaminoacetoacetal, vinylpiperidylacetoacetal-vinyl acetate copolymer, polyvinylacetal diethylaminoacetate, polydiethylaminoethylmethacrylate, polydiethylaminomethylstyrene, polyvinylethylpyridine, vinylethylpyridine-styrene copolymer, vinylethylpyridine-acrylonitrile copolymer, methylvinylpyridineacrylonitrile copolymer and methylvinylpyridine-styrene copolymer; nitrogen-containing polysaccharides such as chitosan and chitin; metal salts of polysaccharide such as calcium alginate; and water-insoluble salts of an acid which is less acidic than hydrochloric acid and is acceptable to a living body such as calcium carbonate, calcium tertiary phosphate, calcium hydrogen phosphate, magnesium tertiary phosphate, zinc phosphate, aluminum phosphate, calcium silicate, calcium pyrophosphate, magnesium carbonate, lead carbonate and cobalt carbonate.

The content of the substance (B) in the surface layer portion may preferably be at least 10% by weight. If the content should be less than 10% by weight, the content of the substance (C) will be increased relatively and therefore the physiologically-active substance will be made difficult to dissolve out in the abomasum of a ruminant, so that a poor effect will be resulted. Further, the substance B may be contained in the internal layer portion (i.e., the portion inside the surface layer portion) without any disadvantages.

The amount of the substance (B) to be used may generally be in the range of 5–90% by weight or preferably 10–80% by weight based on the total amount of said granules.

Further, the content in the surface layer portion of at least one substance (C) selected from the group consisting of straight-chain or branched, saturated or unsaturated, monocarboxylic acids having at least 14 carbon atoms and salts thereof, animal fats having a melting point of 40° C. or higher, vegetable fats having a melting point of 40° C. or higher and waxes having a melting point of 40° C. or higher may preferably be less than 90% by weight. If the content should be 90% by weight or higher, the physiologically-active substance will be rendered difficult to dissolve out in the abomasum of a ruminant and thus a poor effect will also be resulted. The substance (C) may be contained in the internal layer portion without any disadvantages.

The amount of the substance (C) to be used may generally be at least 10% by weight based on the total amount of the granules to be produced. Any amounts less than 10% by weight tend to impair the stability of the physiologically-active substance to a considerable extent even under neutral condition so that no significant effects will be brought about. If excessively large amount of the substance (C) should be used, there will be raised such problems that the content of effective substances will correspondingly be lowered and their dissolution even at a pH of less than 3 will be rendered difficult. Thus, satisfactory effects will not be produced.

In the present invention, it is possible to admix properly one or more fourth ingredients for various purposes in addition to the aforementioned substances (A), (B) and (C). Specific examples of the fourth ingredient may include binder, density adjusting agent, extending agent, taste modifier, lubricant and the like.

The granules containing physiologically-active substance in accordance with the present invention are produced in the following manner.

In the first method, granules containing at least the substances (A), (B) and (C) are subjected to a heat treatment to treat only the surface thereof at a temperature above the melting point of the substance (C), thereby forming a protective film on the surface of the granules. In this method, it is necessary in the first place to prepare granules containing at least the substances (A), (B) and (C). Any conventional granulation processes and granular shape well-known in the art may be used respectively as the granulation process and the shape of the granules containing the substances (A), (B) and (C), or further containing the fourth ingredients.

As processes useful for granulating the granules, there may be mentioned conventional processes of, for example, rolling granulation, extrusion granulation, compaction granulation, fluidizing granulation, crushing granulation, agitation granulation and the like. Further, the granule may have the shape of pellet, granule, rectangular granule, tablet or the like.

This method can be established by subjecting granules containing at least the substances (A), (B) and (C) to a heat treatment to treat only the surface thereof at a temperature above the melting point of the substance (C). The "heat treatment" as used herein is to expose the granules to a predetermined temperature. Although some effects are observed only by subjecting the granules to a heat treatment under the state of standing, more efficient results will be obtained by subjecting the granules to a heat treatment under fluidization or vibration. As the process of fluidization or vibration, any prior art processes are used and they may be applied in such a manner that the granules containing at least the substances (A), (B) and (C) may not be broken. The time duration of the heat treatment is dependent on the melting point of the substance (C) and the temperature of the heat treatment and therefore cannot be specified generally. However, if the time duration is too short, no films will be formed on the surface, while on the other hand, if it is too long, the whole granules will undergo the heat treatment.

In the second method, granules containing at least the substances (A) and (C) are prepared at first and the resulting granules are subjected to a heat treatment at a temperature higher than the melting point of the substance (C) in the presence of the substance (B), thereby forming a protective film on the surface of the granules. In this method, it is necessary to prepare granules containing at least the substances (A) and (C) in the same manner as in the first method. The granules may contain the foregoing fourth substance or substances and/or may contain a portion of the substance (B). The granulation is carried out in the same manner as in the first method.

This method can be established by subjecting the surface of granules containing at least the substances (A) and (C) to a heat treatment at a temperature higher than the melting point of the substance (C) in the coexistence of the substance (B). The "heat treatment" as used herein is to expose the granules to a predetermined temperature and is not limited by the process of heat treatment.

The time duration for the heat treatment is dependent on the melting point of the substance (C) and the temperature of the heat treatment and therefore cannot be specified generally. However, if the time duration is too short, sufficient film may not be formed and therefore it is generally preferred to conduct the heat treatment at least for one minute. Although some effects are observed even when the granules are subjected to a heat treatment under a standing state, more improved effects can be obtained by subjecting the granules to the heat treatment under fluidization or vibration. The fluidization or vibration is effected for the purpose of coating uniformly at least the substance (B) over the granules containing at least the substances (A) and (C) and is not limited by its method, intensity and the like. Any prior art processes can be used as the method of fluidization or vibration. As regards the intensity, the fluidization or vibration is effected to such a extent that the granules containing at least the substances (A) and (C) may not be broken.

The amount of the coexisting substance (B) may generally be in the range of 5–80 parts by weight or preferably 8–70 parts by weight based on 100 parts by weight of the granule containing at least the substances (A) and (C). If the amount of the coexisting substance (B) is downwards of aforesaid lower limit, sufficient coating will not be produced and the stability of the physiologically-active substance will be impared even under neutral condition, so that satisfactory effects will not be obtained. If the amount of the coexisting substance (B) is in excess of the aforesaid upper limit, the amount of the effective substances will be decreased relatively and the dissolution of the physiologically-active substance will be impaired even under acidic condition, so that satisfactory effects will not also be obtained.

In the third method, granules containing at least the substances A and C are prepared at first in the same manner as in the second method. Thereafter, the resulting granules are coated with at least the substance (B) by means of pan coating, fluidizing coating, dry coating or the like, or by use of capsules.

As described above, the granules coated at the surface layer portion thereof with a protective film comprising at least 10% by weight of the substance (B) and at most 90% by weight of the substance (C) can be used as a feed additive composition. Animals to which the feed additive composition is fed are, in particular, ruminants, specific examples of which are beef cattle, dairy cattle, calves, sheep, goats and the like.

Using this feed additive composition, the physiologically-active substance or substances contained therein are passed through the rumen of a ruminant substantially unaltered and dissolved out and absorbed in the abomasum thereof, so that the ruminants can efficiently utilize the useful substances.

Since the granules containing physiologically-active substance in accordance with the present invention are satisfactorily stable under neutral condition and allow the physiologically-active substance or substances contained therein to dissolve at a pH of 3 or less, they are particularly useful as granules for use as a feed additive composition for animals. Further, being composed of simple steps and capable of selecting the substances (B) and (C) in a proper manner, the method for preparing the granules in accordance with the present invention is very useful.

The present invention will be illustrated more specifically by the following Examples and Comparative Examples. All designations of "part or parts" and "%" in Examples and Comparative Examples mean part or parts by weight and % by weight respectively.

EXAMPLES 1–5 & COMPARATIVE EXAMPLES 1 AND 2

After intimately mixing in a ribbon mixer DL-methionine, calcium tertiary phosphate, stearic acid and methyl cellulose (only in Example 4) at their respective proportions given in Table 1, pellets of 2 mm across and 3 mm long were produced using a pelletizer. The resulting pellets were then subjected to a heat treatment in a rotary evaporator under the conditions given in Table 1. The pellets thus prepared were heat-treated only on their surfaces, and the leaching tests of the pellets conducted in a neutral solution (0.1M sodium phosphate buffer, pH 7.0) and an acidic solution (0.1N hydrochloric acid) gave the results shown in Table 1.

Each of the leaching tests was carried out in the following manner. 5 g of the above-prepared pellets was immersed in 100 ml of the neutral or acidic solution in an Erlenmeyer flask. After shaking it at 37° C. on a shaker for a predetermined time period, the amount of DL-methionine leached out from the pellets into the corresponding solution was measured by the iodometric titration method. The shaking time was set at 10 hours in the case of the neutral solution and at 3 hours in the case of the acidic solution.

Compositions, heat-treatment conditions and results of the leaching tests in the Examples and Comparative Examples are summarized in Table 1. In this table, Comparative Example 1 illustrates the case in which no heat treatment was conducted at all and Comparative Example 2 gives the case in which the heat treatment was effected not only on the surface of the granules but also in the interior thereof. In these Examples, stearic acid is the at least one substance selected from the foregoing category (C). Since stearic acid has a melting point of 70.1° C., the temperatures of the heat treatment were set at 90° C. or 120° C.

EXAMPLES 6 AND 7 & COMPARATIVE EXAMPLES 3 AND 4

In the same manner as in the foregoing Examples and Comparative Examples, pellets containing L-lysine hydrochloride, calcium carbonate and 54° C. hydrogenated oil were prepared and subjected to a heat treatment. The amount of leached-out L-lysine hydrochloride was determined by means of the ninhydrin colorimetry. Compositions, heat-treatment conditions, and results of the leaching tests are summarized in Table 2.

EXAMPLE 8

In the same manner as in Example 1, pellets containing L-lysine hydrochloride, calcium carbonate and candelila wax were prepared and subjected to a heat treatment. The amount of leached-out L-lysine hydrochloride was determined by means of the ninhydrin colorimetry. Compositions, heat-treatment conditions and results of the leaching test are summarized in Table 3.

EXAMPLE 9

In the same manner as in Examples 1–5, pellets comprising nicotinic acid amide, dimethylamino cellulose, 54° C. hydrogenated oil were prepared and subjected to a heat treatment. The amount of leached-out nicotinic acid amide was determined by measuring the N-content in accordance with the Kjeldahl method. Compositions, heat-treatment conditions and results of the leaching test are summarized in Table 4.

EXAMPLES 10–19 & COMPARATIVE EXAMPLES 5 AND 6

After intimately mixing in a ribbon mixer DL-methionine, stearic acid and sodium polyacrylate (only in Example 13) at their respective proportions given in Table 5, pellets of 2 mm across and 3 mm long were prepared using a pelletizer. 100 parts of the pellets thus obtained and calcium tertiary phosphate in amounts given in Table 5 were fed into a rotary evaporator, in which the resulting mixture was then subjected to a heat treatment while rotating under the conditions given in Table 5.

Using the pellets prepared in the foregoing manner, leaching tests were conducted in a neutral solution (0.1M sodium phosphate buffer, pH 7.0) and an acidic solution (0.1N hydrochloric acid). Each of the leaching tests was carried out in the following manner. Namely, 5 g of the above-prepared pellets was immersed in 100 ml of the neutral or acidic solution placed in an Erlenmeyer flask. After shaking it at 37° C. on a shaker for a predetermined period of time, the amount of DL-methionine leached out from the pellets into the corresponding solution was measured by the iodometric titration method. The shaking time was set at 10 hours for the neutral solution and at 3 hours for the acidic solution.

Composition, heat-treatment conditions and results of the leaching tests are summarized in Table 5.

EXAMPLE 20

Pellets containing L-lysine hydrochloride and 54° C. hydrogenated oil were prepared in the same manner as in Examples 10–19. 100 parts of the pellets and 30 parts of calcium carbonate were fed into a rotary evaporator, in which the resulting mixture was subjected to a heat treatment under rotation. The amount of leached-out L-lysine hydrochloride was determined by means of the ninhydrin colorimetry. Composition, heat-treatment conditions and results of the leaching tests were summarized in Table 6.

EXAMPLE 21

After intimately mixing in a ribbon mixer nicotinic acid amide and 54° C. hydrogenated oil at their respective proportions given in Table 7, spherical granules having 2 mm of diameter were prepared using a spherical granulator. 100 parts of the spherical granules and 30 parts of diamino cellulose were fed into a rotary evaporator, in which the resulting mixture was subjected to a heat treatment under rotation. The amount of leached-out nicotinic acid amide was determined by measuring the N content in each solution in accordance with the Kjeldahl method. Compositions, heat-treatment conditions and results of the leaching test are summarized in Table 7.

EXAMPLES 22–25 & COMPARATIVE EXAMPLE 7

After intimately mixing in a ribbon mixer DL-methionine (A), 54° C. hydrogenated oil (C) and carboxymethyl cellulose as a binder at their respective proportions given Table 8, spherical granules having a diameter of 3 mm were prepared using a granulator. Then, 100 parts of the resulting granules and calcium bicarbonate (B) in amounts given in Table 8 were fed into a rotary evaporator, in which the resulting mixture was subjected to a heat treatment at 90° C. for 40 minutes under rotation. Coating of the spherical granules was thus completed. Using the thus-obtained granular feed additive composition, leaching tests were conducted on DL-methionine in an artificial ruminal juice and an artificial abomasal juice, and the compositions of each layer of the prepared spherical granule were analyzed.

As the artificial ruminal juice used in the leaching tests of DL-methionine, there was used a 0.1M sodium phosphate buffer. On the other hand, a 0.1N hydrochloric acid was employed as the artificial abomasal juice. Each of the leaching tests was carried out in the following manner. Namely, 5 g of the above-prepared spherical feed additive granules was immersed in 100 ml of the artificial ruminal or abomasal juice placed in a 300 ml-Erlenmeyer flask and then maintained at 37° C. on a shaker. After shaking the resulting mixture for a predetermined period of time, the amount of DL-methionine leached out from the granules into the corresponding juice was measured by the iodometric titration method. The shaking time was set at 10 hours for the artificial ruminal juice and at 3 hours for the artificial abomasal juice.

Analysis of the compositions of each layer of the spherical granule was conducted as follows. Each of 50 spherical granules prepared was cut into two pieces and about 0.5 g of sample was taken using a pincette from each of the portion accounting for 20% of the granular diameter from the surface of the granule and the portion inside the former portion so as to be subjected to analysis. The amount of fat was determined by the ester value method, that of calcium bicarbonate by the atomic absorption method, and that of DL-methionine by the iodometric titration method. Compositions, results of the leaching test and analysis results of the each layer compositions in the Examples and Comparative Example are summarized in Table 8. The analysis results of the each layer compositions are expressed such that the amounts of the three components other than the binder are sum up to 100, although the binder was not analyzed.

EXAMPLES 26 AND 27

After intimately mixing in a ribbon mixer L-lysine hydrochloride (A) and palm hardened oil (C) at their respective proportions given in Table 9, spherical granules having a diameter of 3 mm were prepared using a granulator. 100 parts of the resulting spherical granules and 30 parts of calcium tertiary phosphate were fed into a fluidizing coating apparatus in which coating of the granules was completed under fluidization while being sprayed with 20 parts of palm hardened oil. Using the granular feed additive compositions thus obtained, leaching tests and analysis of the each layer of spherical granules were carried out in the same manner as in Example 22. The amount of leached-out L-lysine hydrochloride was determined by means of the ninhydrin colorimetry. The compositions were analysed by the ninhydrin colorimetry for L-lysine hydrochlode, by the atomic absorption method for calcium tertiary phosphate, and by the ester value method for palm hardened oil. Results are summarized in Table 9.

TABLE 1

| Example & Comparative Example | Compositions | | | | Heat-treatment conditions | | Leached-out methionine | |
|---|---|---|---|---|---|---|---|---|
| | DL-methionine (%) | Calcium tertiary phosphates (%) | Stearic acid (%) | Methyl cellulose (%) | Temperature (°C.) | Time (minute) | In neutral solution (%) | In acidic solution (%) |
| Example | | | | | | | | |
| 1 | 30 | 30 | 40 | — | 90 | 10 | 10 | 81 |
| 2 | 30 | 30 | 40 | — | 90 | 60 | 8 | 80 |
| 3 | 30 | 30 | 40 | — | 120 | 30 | 8 | 81 |
| 4 | 20 | 65 | 13 | 2 | 90 | 40 | 7 | 85 |
| 5 | 35 | 15 | 50 | — | 90 | 40 | 9 | 79 |
| Comparative Example | | | | | | | | |
| 1 | 30 | 30 | 40 | — | — | — | 18 | 78 |
| 2 | 30 | 30 | 40 | — | 150 | 360 | 2 | 6 |

TABLE 2

| Example & Comparative Example | Compositions | | | Heat-treatment conditions | | Leached-out L-lysine hydrochloride | |
|---|---|---|---|---|---|---|---|
| | L-lysine hydrochloride (%) | Calcium carbonate (%) | 54° C. hydrogenated oil (%) | Temperature (°C.) | Time (minute) | In neutral solution (%) | In acidic solution (%) |
| Example | | | | | | | |
| 6 | 30 | 30 | 40 | 80 | 60 | 10 | 77 |
| 7 | 20 | 40 | 40 | 80 | 60 | 9 | 79 |
| Comparative Example | | | | | | | |
| 3 | 30 | 30 | 40 | — | — | 18 | 76 |
| 4 | 30 | 30 | 40 | 100 | 360 | 3 | 8 |

TABLE 3

| | Compositions | | | Heat-treatment conditions | | Leached-out L-lysine hydrochloride | |
|---|---|---|---|---|---|---|---|
| Example | L-lysine hydrochloride (%) | Calcium carbonate (%) | Candelila wax (%) | Temperature (°C.) | Time (minute) | In neutral solution (%) | In acidic solution (%) |
| 8 | 30 | 30 | 40 | 90 | 60 | 13 | 79 |

TABLE 4

| | Compositions | | | Heat-treatment conditions | | Leached-out L-lysine hydrochloride | |
|---|---|---|---|---|---|---|---|
| Example | Nicotinic acid amide (%) | Dimethyl-amino cellulose (%) | 54° C. hydrogenated oil (%) | Temperature (°C.) | Time (minute) | In neutral solution (%) | In acidic solution (%) |
| 9 | 30 | 30 | 40 | 80 | 60 | 11 | 82 |

TABLE 5

| Example & Comparative Example | Composition | | | | Heat-treatment conditions | | Leached-out methionine | |
|---|---|---|---|---|---|---|---|---|
| | DL-methionine (%) | Stearic acid (%) | Sodium polyacrylate (%) | Calcium tertiary phosphate (part) | Temperature (°C.) | Time (minute) | In neutral solution (%) | In acidic solution (%) |
| Example | | | | | | | | |
| 10 | 50 | 50 | — | 10 | 90 | 60 | 15 | 85 |
| 11 | 50 | 50 | — | 30 | 90 | 60 | 8 | 82 |
| 12 | 50 | 50 | — | 50 | 90 | 60 | 3 | 60 |
| 13 | 50 | 48 | 2 | 30 | 90 | 60 | 5 | 80 |
| 14 | 50 | 50 | — | 30 | 90 | 5 | 12 | 88 |
| 15 | 50 | 50 | — | 30 | 90 | 30 | 10 | 85 |
| 16 | 50 | 50 | — | 30 | 90 | 120 | 7 | 81 |
| 17 | 20 | 80 | — | 30 | 90 | 60 | 5 | 63 |
| 18 | 65 | 35 | — | 30 | 90 | 60 | 13 | 92 |
| 19 | 50 | 50 | — | 30 | 120 | 30 | 8 | 83 |
| Comp. Ex. | | | | | | | | |
| 5 | 50 | 50 | — | — | — | — | 82 | 96 |
| 6 | 50 | 50 | — | — | 90 | 60 | 25 | 27 |

TABLE 6

| | Compositions | | | Heat-treatment conditions | | Leached-out L-lysine hydrochloride | |
|---|---|---|---|---|---|---|---|
| Example | L-lysine hydrochloride (%) | 54° C. hydrogenated oil (%) | Calcium carbonate (part) | Temperature (°C.) | Time (minute) | In neutral solution (%) | In acidic solution (%) |
| 20 | 50 | 50 | 30 | 100 | 30 | 5 | 88 |

TABLE 7

| | Compositions | | | Heat-treatment conditions | | Leached-out nicotinic acid amide | |
|---|---|---|---|---|---|---|---|
| Example | Nicotinic acid amide (%) | 54° C. hydrogenated oil (%) | Diamino cellulose (part) | Temperature (°C.) | Time (minute) | In neutral solution (%) | In acidic solution (%) |
| 21 | 50 | 50 | 30 | 100 | 30 | 8 | 87 |

TABLE 8

| Example & Comparative Example | Compositions | | | | Leached-out[*1] DL-methionine | | Surface layer content | | | Internal layer content | | |
|---|---|---|---|---|---|---|---|---|---|---|---|---|
| | A (part) | C (part) | Binder (part) | B (part) | Artificial ruminal juice (%) | Artificial abomasal juice (%) | A (%) | C (%) | B (%) | A (%) | C (%) | B (%) |
| Example | | | | | | | | | | | | |
| 22 | 50 | 50 | 0.5 | 30 | 7 | 84 | 2 | 30 | 68 | 50 | 46 | 4 |
| 23 | 70 | 30 | 0.5 | 30 | 8 | 86 | 4 | 25 | 69 | 67 | 24 | 9 |
| 24 | 70 | 30 | 0.5 | 50 | 5 | 83 | 2 | 22 | 76 | 68 | 21 | 11 |
| 25 | 50 | 50 | 0.5 | 7 | 3 | 70 | 2 | 81 | 17 | 49 | 48 | 3 |
| Comparative Example | | | | | | | | | | | | |

TABLE 8-continued

| Example & Comparative Example | Compositions | | | | Leached-out(*1) DL-methionine | | Surface layer content | | | Internal layer content | | |
|---|---|---|---|---|---|---|---|---|---|---|---|---|
| | A (part) | C (part) | Binder (part) | B (part) | Artificial ruminal juice (%) | Artificial abomasal juice (%) | A (%) | C (%) | B (%) | A (%) | C (%) | B (%) |
| 7 | 50 | 50 | 0.5 | 3 | 3 | 27 | 1 | 93 | 6 | 47 | 49 | 4 |

(*1)Expressed in terms of % of leached-out DL-methionine based on the whole DL-methionine.

TABLE 9

| | Compositions | | | Leached-out(*1) L-lysine hydrochloride | | Surface layer content | | | Internal layer content | | |
|---|---|---|---|---|---|---|---|---|---|---|---|
| Example | A (%) | C (%) | B (part) | Artificial ruminal juice (%) | Artificial abomasal juice (%) | A (%) | C (%) | B (%) | A (%) | C (%) | B (%) |
| 26 | 40 | 60 | 30 | 5 | 81 | 1 | 67 | 32 | 38 | 58 | 4 |
| 27 | 70 | 30 | 30 | 7 | 83 | 6 | 59 | 35 | 68 | 27 | 5 |

(*1)Expressed in terms of % of leached-out L-lysine hydrochloride based on the whole L-lysine hydrochloride.

What is claimed is:

1. In a method for preparing a granule containing physiologically-active substance which contains at least:
   (A) a physiologically-active substance;
   (B) a substance which is stable under neutral conditions but disintegrates or dissolves at a pH of 3 or less, said substance being selected from the group consisting of cellulose derivatives, polyvinyl derivatives, nitrogen-containing polysaccharides, metal salts of a polysaccharide and water-insoluble salts of an acid which is less acidic than hydrochloric acid and is acceptable to a living body, the amount of said substance ranging from 5 to 90 percent by weight based on the total amount of the granule; and
   (C) at least one substance selected from the group consisting of straight-chain or branched, saturated or unsaturated monocarboxylic acids having 14 carbon atoms or more and salts thereof, animal fats having a melting point of 40° C. or higher, vegetable fats having a melting point of 40° C. or higher and waxes having a melting point of 40° C. or higher, the improvement which comprises subjecting said granule to a heat treatment to treat only the surface thereof at temperature higher than the melting point of said substance (C), thereby forming a protective film containing at least said substance (B) and (C) on the surface thereof.

2. In a method for preparing a granule containing physiologically-active substance which contains at least:
   (A) a physiologically-active substance;
   (B) a substance which is stable under neutral conditions but disintegrates or dissolves at a pH of 3 or less, said substance being selected from the group consisting of cellulose derivatives, polyvinyl derivatives, nitrogen-containing polysaccharides, metal salts of a polysaccharide and water-insoluble salts of an acid which is less acidic than hydrochloric acid and is acceptable to a living body, the amount of said substance ranging from 5 to 90 percent by weight based on the weight of the granule containing at least the substances (A) and (C); and
   (C): at least one substance selected from the group consisting of straight-chain or branched, saturated or unsaturated monocarboxylic acids having 14 carbon atoms or more and salts thereof, animal fats having a melting point of 40° C. or higher, vegetable fats having a melting point of 40° C. or higher and waxes having a melting point of 40° C. or higher, the improvement which comprises subjecting a granule which has been previously prepared and contains at least said substances (A) and (C) to a heat treatment to treat the surface thereof at a temperature higher than the melting point of said substance (C) in the presence of said substance (B).

3. Method for preparing a feed additive composition capable of passing through the rumen substantially unaltered and of dissolving in the abomasum of ruminants which comprises granulating a mixture containing at least:
   (A) a physiologically-active substance;
   (B) a substance which is stable under neutral conditions but disintegrates or dissolves at a pH 3 or less, said substance being selected from the group consisting of cellulose derivatives, polyvinyl derivatives, nitrogen-containing polysaccharides, metal salts of a polysaccharide and water-insoluble salts of an acid which is less acidic than hydrochloric acid and is acceptable to a living body, the amount of said substance ranging from 5 to 90 percent by weight based on the amount of the granule; and
   (C) at least one substance selected from the group consisting of straight-chain or branched, saturated or unsaturated monocarboxylic acids having 14 carbon atoms or more and salts thereof, animal fats having a melting point of 40° C. or higher, vegetable fats having a melting point of 40° C. or higher and waxes having a melting point of 40° C. or higher and then subjecting the resultant granule to a heat treatment to treat only the surface thereof at a temperature higher than the melting point of said substance (C) long enough to form a protective film containing at least said substances (B) and (C) on the surface thereof.

4. Method for preparing a feed additive composition capable of passing through the rumen substantially unaltered and of dissolving in the abomasum of ruminants which comprises granulating a mixture containing at least:
   (A) physiologically-active substance;
   (C) at least one substance selected from the group consisting of straight-chain or branched, saturated or unsaturated monocarboxylic acids having 14 carbon atoms or more and salts thereof, animal fats having a melting point of 40° C. or higher, vegetable fats having a melting point of 40° C. or higher and waxes having a melting point of 40° C. or higher; and subjecting the resultant granule to a heat treatment to treat only the surface thereof at a temperature higher than the melting point of said substance (C) in the presence of a substance (B) which is stable under neutral conditions but disintegrates or dissolves at a pH 3 or less, said substance being selected from the group consisting of cellulose derivatives, polyvinyl derivatives, nitrogen-containing polysaccharides, metal salts of a polysaccharide and water-insoluble salts of an acid which is less acidic than hydrochloric acid and is acceptable to a living body, the amount of said substance ranging from 5 to 80 percent by weight based on the weight of the granule containing at least the substances (A) and (B), thereby forming a film on the surface of the granule.

5. The method as claimed in claim 3 wherein the temperature ranges from 80° to 120° C. and the time ranges from 10 to 60 minutes.

6. The method as claimed in claim 4 wherein the temperature ranges from 90° to 120° C. and the time ranges from 5 to 120 minutes.

* * * * *